United States Patent
Majeed et al.

(10) Patent No.: US 10,235,728 B1
(45) Date of Patent: Mar. 19, 2019

(54) INTEGRATED MEDICAL PRACTICE MANAGEMENT AND IMAGE MANAGEMENT

(75) Inventors: Christina M. Majeed, Tampa, FL (US); Donald R. Thompson, Tampa, FL (US); Christopher A. Haag, Tampa, FL (US); Kamal N. Majeed, Tampa, FL (US); Samer Dohle, Tampa, FL (US)

(73) Assignee: NexTech Systems, Inc., Tampa, FL (US)

( * ) Notice: Subject to any disclaimer, the term of this patent is extended or adjusted under 35 U.S.C. 154(b) by 600 days.

(21) Appl. No.: 12/708,143

(22) Filed: Feb. 18, 2010

(51) Int. Cl.
*G06Q 50/22* (2018.01)
*G16H 10/60* (2018.01)

(52) U.S. Cl.
CPC ............ *G06Q 50/22* (2013.01); *G16H 10/60* (2018.01)

(58) Field of Classification Search
CPC ...... G06Q 50/24; G06Q 50/22; G06F 19/321; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00

USPC ........................................................ 705/2, 3
See application file for complete search history.

(56) References Cited

U.S. PATENT DOCUMENTS

| | | | | |
|---|---|---|---|---|
| 7,403,123 | B2 * | 7/2008 | Robinson | G06Q 50/22 340/573.1 |
| 2002/0012070 | A1 * | 1/2002 | Furui | H01J 31/12 348/566 |
| 2007/0174079 | A1 * | 7/2007 | Kraus | G06Q 10/10 705/3 |
| 2009/0054755 | A1 * | 2/2009 | Shiibashi | G06F 19/321 600/407 |
| 2010/0121581 | A1 * | 5/2010 | Hyde | G01N 33/94 702/19 |

* cited by examiner

*Primary Examiner* — Joy Chng
(74) *Attorney, Agent, or Firm* — Eversheds-Sutherland (US) LLP (57) ABSTRACT

A novel integration of practice management and photo management systems that also integrates patients' electronic medical records to provide a complete software solution for a medical practice. The present invention includes a method of patient image management comprising importing an image having an assigned date, filtering a patient list by appointments that occur on the assigned date, associating the image with a patient from the patient list, retrieving procedure information associated with the patient's appointment, and tagging the image with the procedure information. A corresponding computer system adapted to manage patient images is also provided.

14 Claims, 13 Drawing Sheets

INTEGRATED MEDICAL PRACTICE MANAGEMENT AND IMAGE MANAGEMENT

FIELD OF INVENTION

This invention relates to medical office practice management, electronic medical records, and photo management.

BACKGROUND

Currently available technology provides the ability to store and archive photos within a photo management database. There is also separate systems available for patient practice management and systems for organizing electronic medical records. However, these software technologies do not provide the ability to properly and automatically link and incorporate medical practice management with a patient's medical record, including photographs.

SUMMARY OF INVENTION

The present invention provides a novel integration of practice management and photo management systems that also integrates patients' electronic medical records to provide a complete software solution for a medical practice. The system automates the integration of practice management and Electronic Medical Record (EMR) data, such as demographic information, appointment information, procedure, and coding/billing information from the time of uploading images to be imported. It also provides efficiency and flexibility with the creation of custom tags and searching for images. The system also provides the ability to edit and manipulate images, including a ghost overlay feature.

The present invention includes a method of patient image management. In an embodiment, the method begins by importing an image. The image has an assigned date, such as the date the image was created or taken (in the case of a photo). The patient list is then automatically filtered by appointments that occur on the assigned date. The photo is automatically integrated with the appointment date of the scheduler. The image is associated with a patient from the patient list and procedure information associated with the patient's appointment is automatically retrieved. The image is then tagged with the procedure information. The method may also include retrieving service codes associated with the patient and tagging the image with the service codes. In addition, the method may further include tagging the image with a custom tag responsive to a request from a user.

The method may further include displaying the image in a film icon. The film icon comprises a center image, a first plurality of side images, each of uniform size and each smaller in size than the center image, aligned in a first column on a first side of the center image, and a second plurality of side images, each of uniform size and each smaller in size than the center image, aligned in a second column on a second side of the center image opposite the first column.

In another embodiment, the method begins by importing a plurality of images, each having an assigned date. A patient list is then filtered by appointments that occur on the assigned date. One or more of the images is associated with one or more patients from the patient list. For each image-patient association, procedure information associated with the patient's appointment is retrieved and the image in the image-patient association is tagged with the procedure information. In addition, for each image-patient association, service codes associated with the patient may be retrieved and the image in the image-patient association tagged with the service codes. The method may also include, for each image-patient association, tagging the image in the image-patient association with a custom tag responsive to a request from the user.

The method may further include organizing the images by procedure using the procedure information tag of each photo.

The present invention also includes a corresponding computer system for managing patient images.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention provides a novel integration of practice management and photo management systems that also integrates patients' electronic medical records to provide a complete software solution for a medical practice. The system automates the integration of practice management and Emergency Medical Record (EMR) data, such as demographic information, appointment information, procedure, and coding/billing information from the time of uploading images to be imported. It also provides efficiency and flexibility with the creation of custom tags and searching for images. The system also provides the ability to edit and manipulate images, including a ghost overlay feature.

Figure 1:
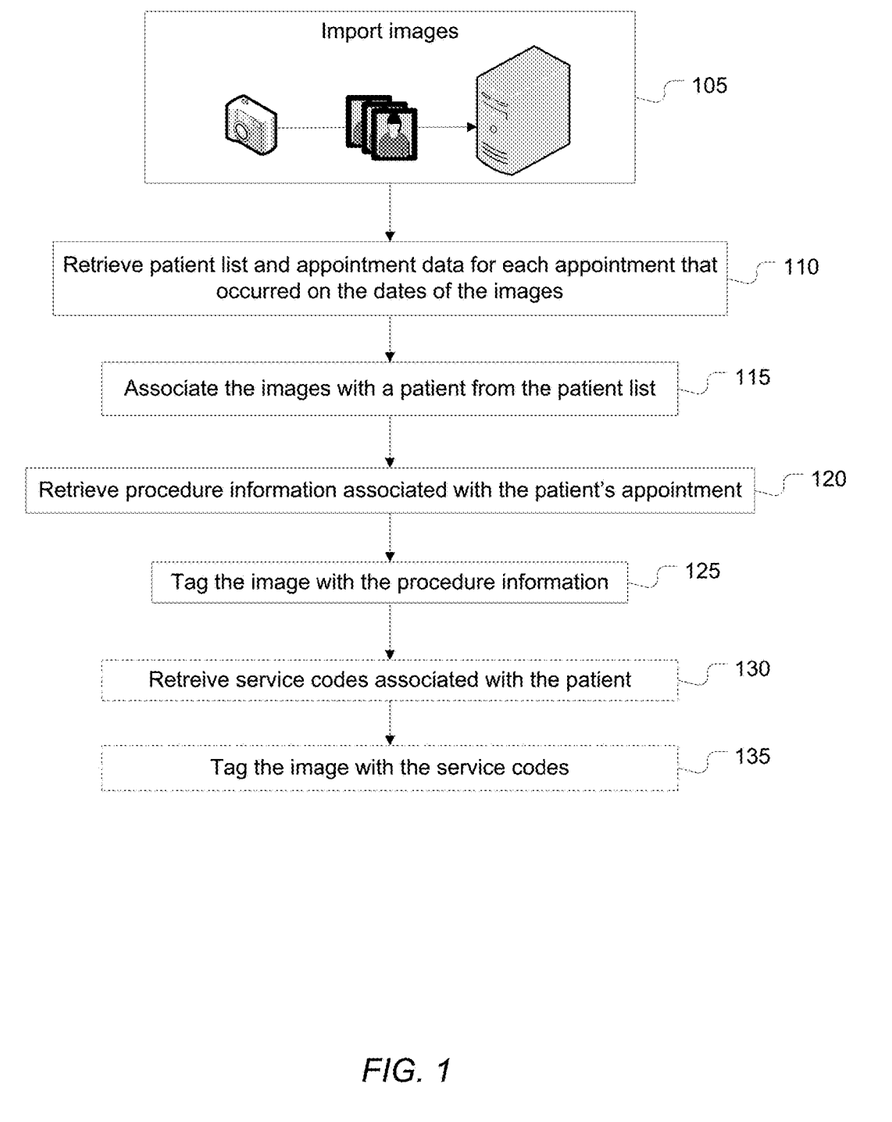
FIG. 1 is a flowchart of the patient image management system according to an embodiment of the present invention.

A flowchart of an embodiment of the patient image management system is shown in FIG. 1. Images, such as photographs, are imported into the system (operation 105). Images may be imported directly from a camera, from a folder stored on the computer, or any other known means. Each of the images includes a label with the date the image was taken. The system allows for importation of multiples images belonging to one or more patients.

Figure 2:
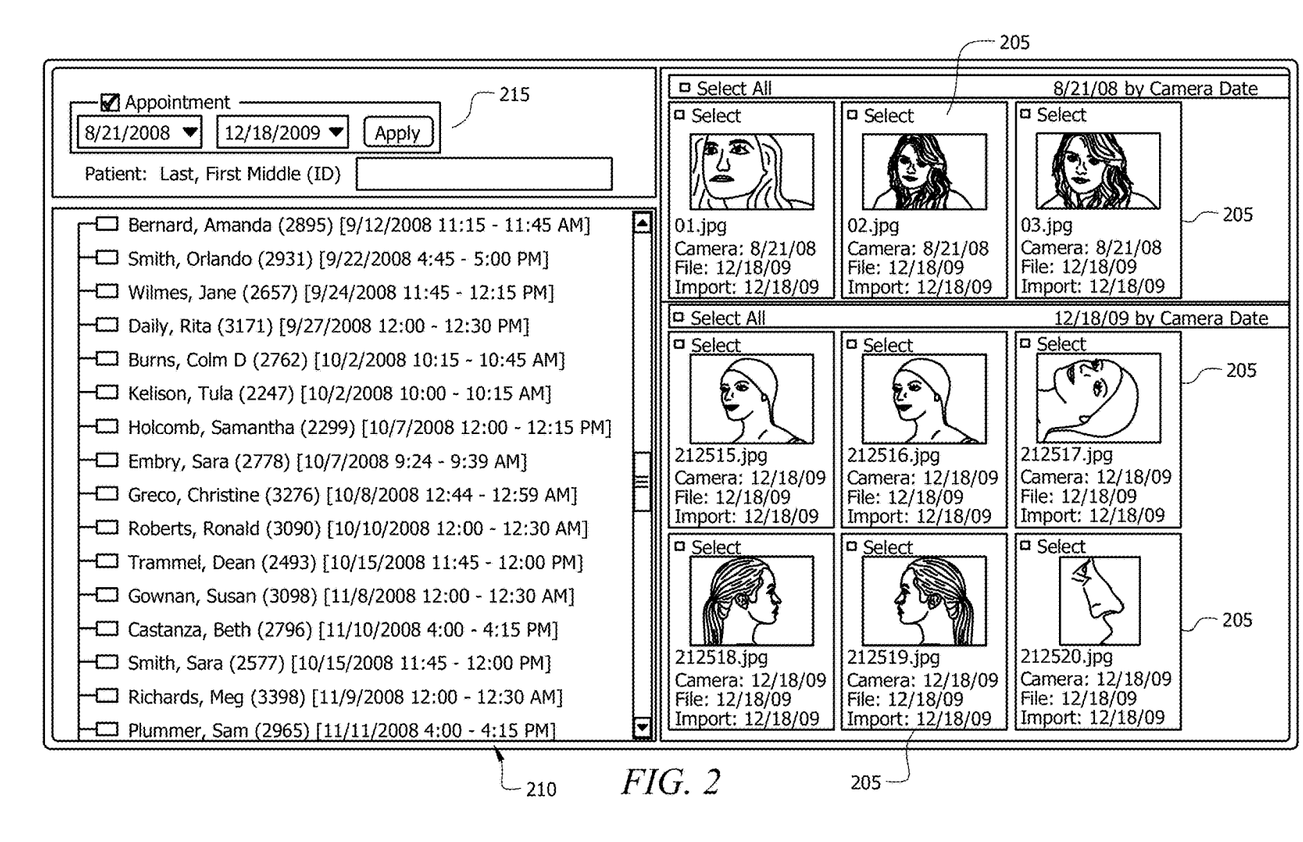
FIG. 2 is a screen shot showing an example of photos imported into the system before they have been associated with a patient (or patient appointment) from the patient list on the left according to an embodiment of the present invention.

Once images are imported, a list of patients that had appointment dates corresponding to the image dates is automatically provided (operation 110). The patient and the patient's appointment also have procedure information (e.g. rhinoplasty, breast augmentation, etc.) associated with them. Service codes and diagnosis codes for information such as fees associated with the patient's appointment(s)/procedure may also be associated with the patient and/or the patient's appointment. FIG. 2 shows an example screen having imported photos 205 sorted by the date the photo was taken on the right side. On the left side is patient list 210, which is a list of patients by their appointment times. Above patient list 210 is filter function 215. When images are imported, the system automatically filters patient list 210 to include those appointments that occurred on the dates the images were taken/created. Filter function 215 can also be used to filter patient list 210 by one or more chosen dates or by patient name.

Once the images have been imported and the patient list has been retrieved, the images are then associated with a patient from the patient list (FIG. 1, operation 115). Patient images can be selected and dragged and dropped to the correct patient name to trigger the system to create the association.

Once images are assigned to the patient, the images are automatically tagged with the patient's procedure information. To do this, the system retrieves procedure information associated with the patient and/or the patient's appointment (FIG. 1, operation 120) and then tags each image associated with the patient with the procedure information (FIG. 1, operation 125).

The patient image management system may also calculate the post-operative interval, the number of days between the date of an appointment and the present date.

The system may also retrieve service codes associated with the patient (FIG. 1, operation 130). The images associated with the patient can then be tagged with these service codes (FIG. 1, operation 135). Custom tags may also be created when importing images. Example custom tags may include Top 10 Rhinoplastys, Facial Fracture Study, Breast Reconstruction Study, etc. Numerous images may be selected at one time. These tagged images can then be re-called by a global search at any point later on.

Figure 3:
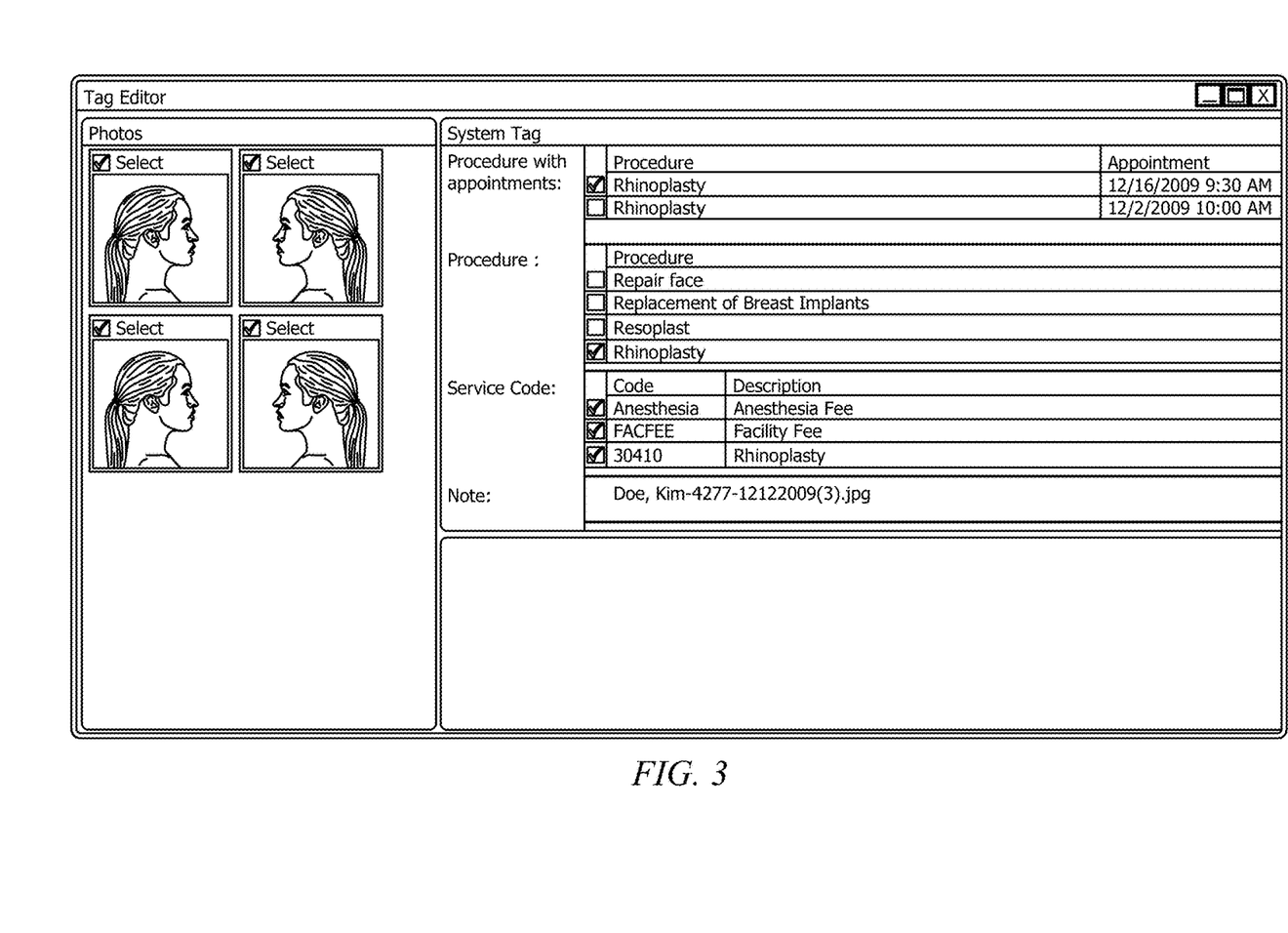
FIG. 3 is a screen shot showing an example tag editing screen according to an embodiment of the present invention.

The tags associated with one or more images can also be edited. FIG. 3 shows an example Tag Editor Screen. In this example, the four photos shown on the left of the screen currently have five tags: a rhinoplasty appointment, a rhinoplasty procedure, and three service codes (i.e. anesthesia fee, facility fee, and rhinoplasty). Tags can be added or removed on this screen.

Figure 4:
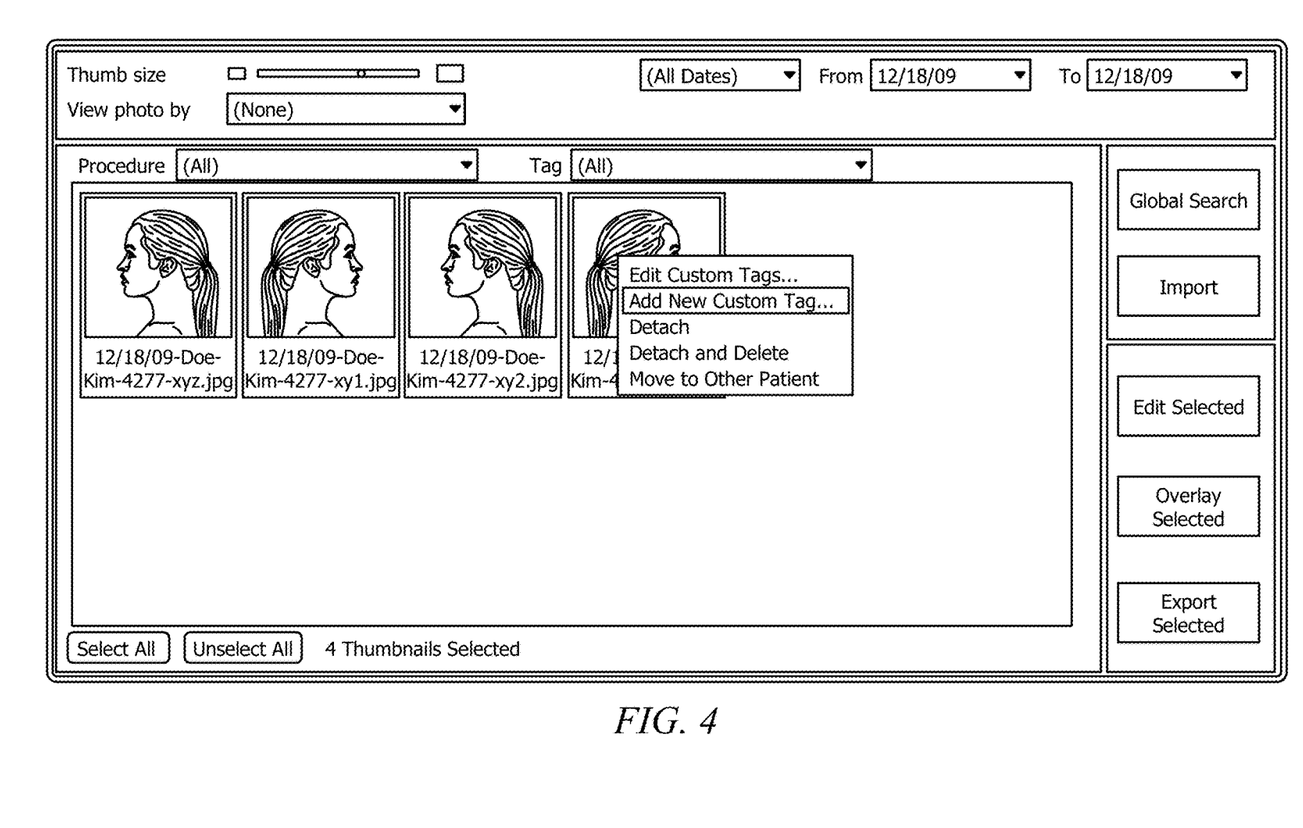
FIG. 4 is a screen shot showing an example patient file and illustrating that custom tags can be created after the images have been imported into the system according to an embodiment of the present invention.
Figure 5:
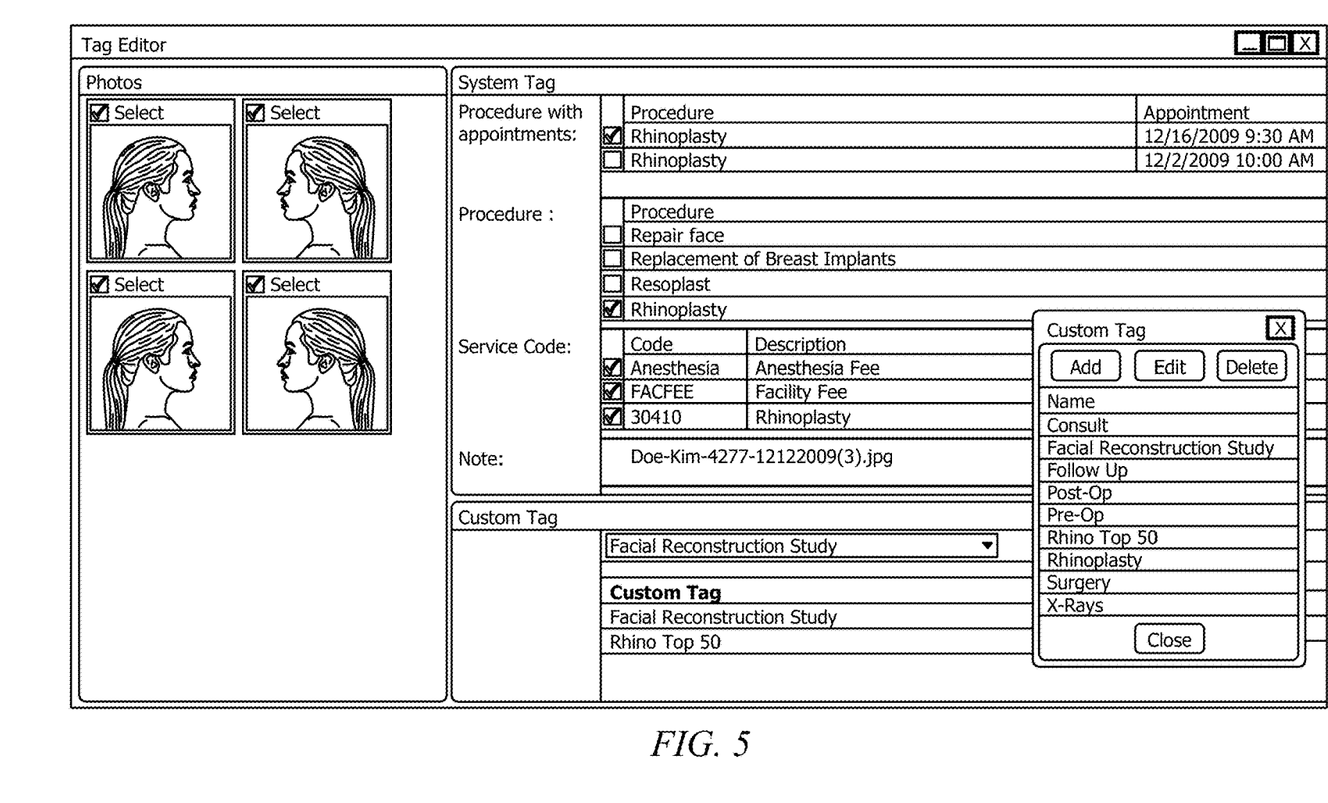
FIG. 5 is a screen shot showing another example of the tag editing screen according to an embodiment of the present invention.
Figure 6:
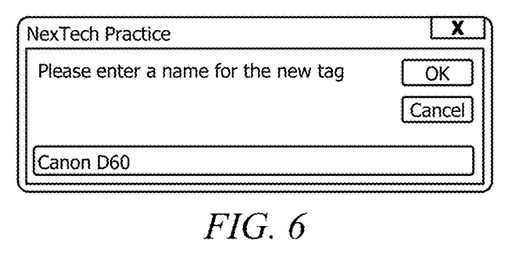
FIG. 6 is a screen shot showing an example of the window used to create a new custom tag according to an embodiment of the present invention.

Custom tags can also be created after the images have been imported into the system. As illustrated in the example screen shown in FIG. 4, the user can select one or more images to create a custom tag for. As illustrated in the example screen shown in FIG. 5, a custom tag can be chosen from a list of existing custom tags or, as shown in FIG. 6, a new custom tag can be created. The selected custom tag or newly created custom tag will then be associated with each selected image.

Figure 7A:
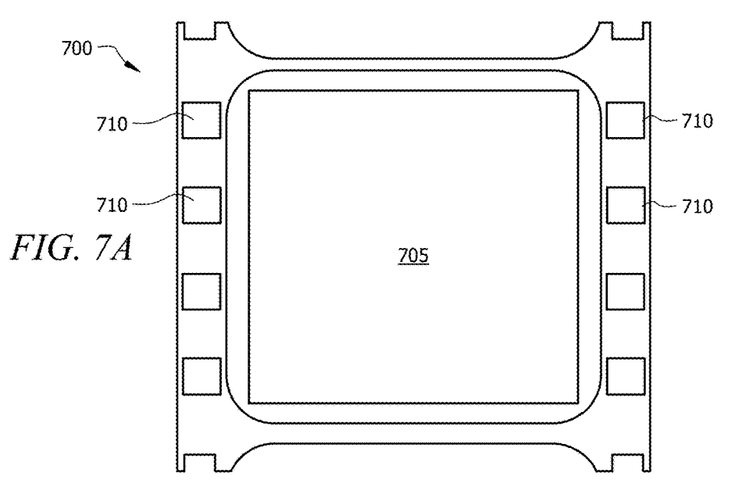
FIG. 7A is an example illustration of the film strip display according to an embodiment of the present invention.
Figure 7B:
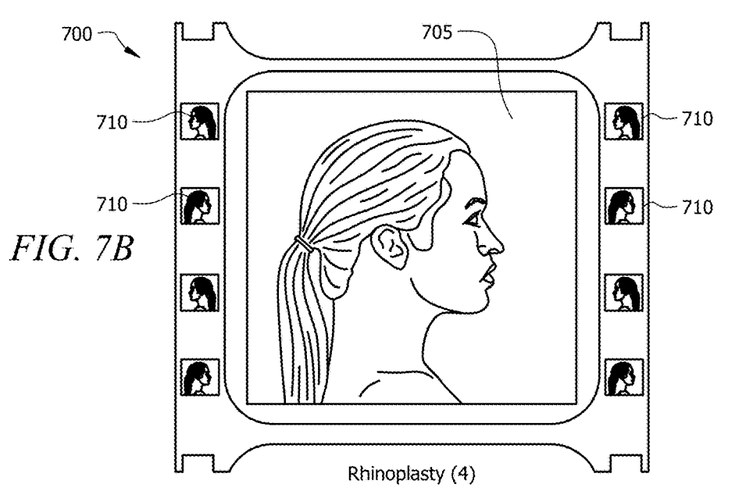
FIG. 7B is an example illustration of the film strip display displaying a plurality of a patient's images according to an embodiment of the present invention.
Figure 7C:
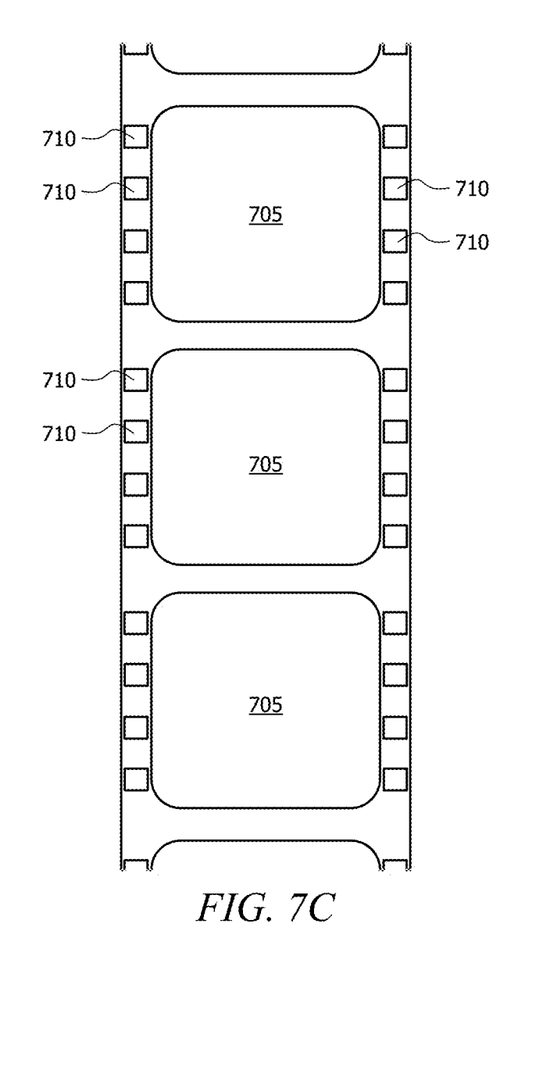
FIG. 7C is an example illustration of an expanded film strip display having multiple center image locations according to an embodiment of the present invention.

Once the images have been associated with a patient's file, the system allows users to organize images by procedure and/or any custom description they see useful. Images may also be displayed in a unique film strip display, as illustrated in FIGS. 7A and 7B. Film strip display 700 includes center image location 705 and plurality of side image locations 710, each of relatively uniform size, aligned along each side of center image location 705. As shown in FIG. 7C, film strip display 700 may be repeated any number of times in a vertical fashion to display any number of images.

Figure 7D:
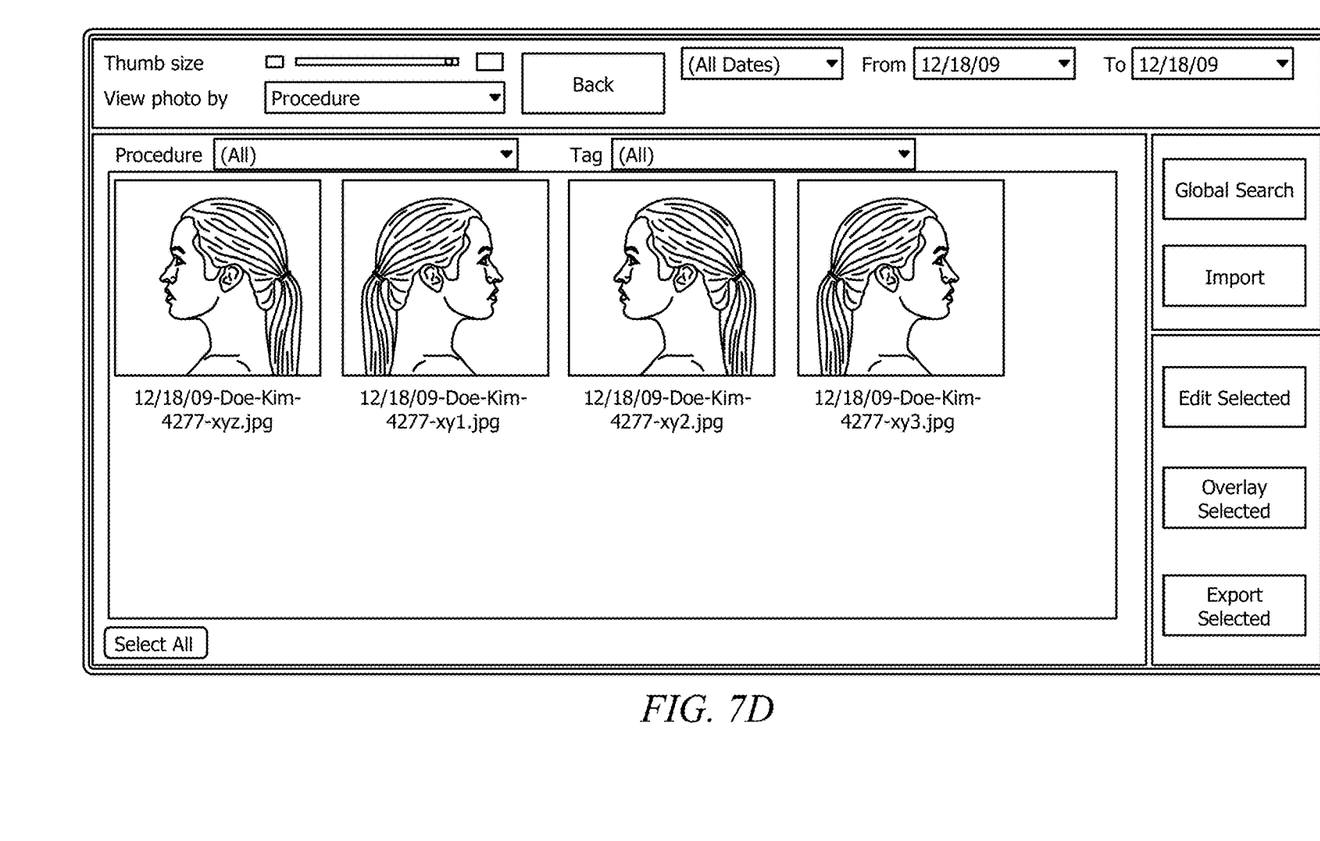
FIG. 7D is a screen shot showing an example of images expanded from the film strip display and displayed in the patient's file according to an embodiment of the present invention.

Center image location 705 may be used to highlight the main image of interest to a user. The name of the group and the number of images within the group may be listed on film strip display 700, as shown in FIG. 7B. New film strip displays can be created and images moved between film strip displays as a way to organize images. New or altered film strip displays can then be stored in the patient's file for later access. Images can also be expanded from film strip display 700 and displayed in the patient's file, as illustrated in FIG. 7D. Film strip display 700 allows users a quick and easy way to drill down and view images, and create sub folders/image filmstrips.

Figure 8:
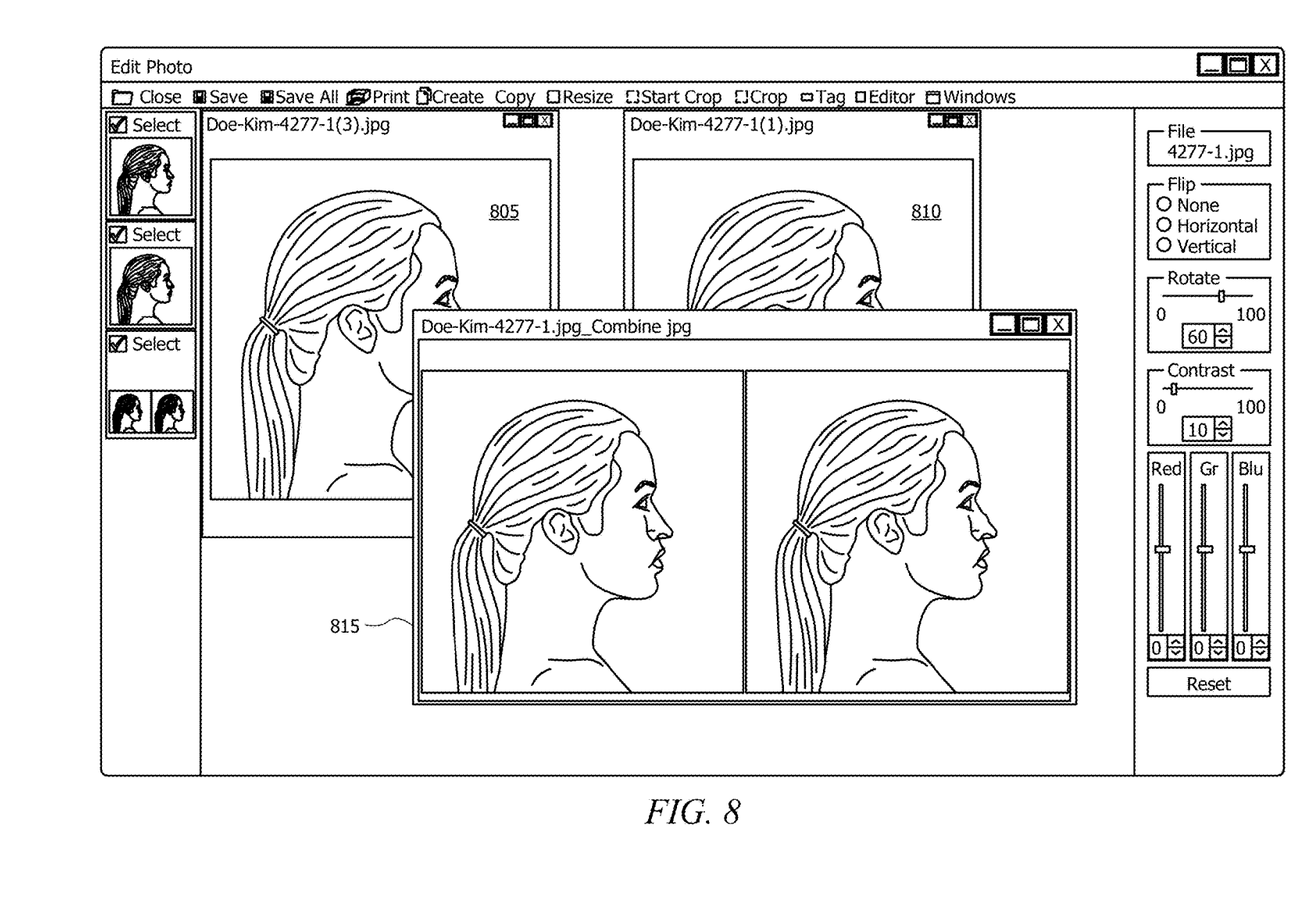
FIG. 8 is a screen shot showing an example of the image editing screen showing creating a single image from two individual images according to an embodiment of the present invention.

The patient image management system also includes numerous editing functions. Multiple images can be combined into a single image. An example is shown in FIG. 8 where pre-op image 805 and post-op image 810 are combined into a single image in comparison image 815. This, among other advantages, allows for an improved demonstration of before and after images.

Figure 9:
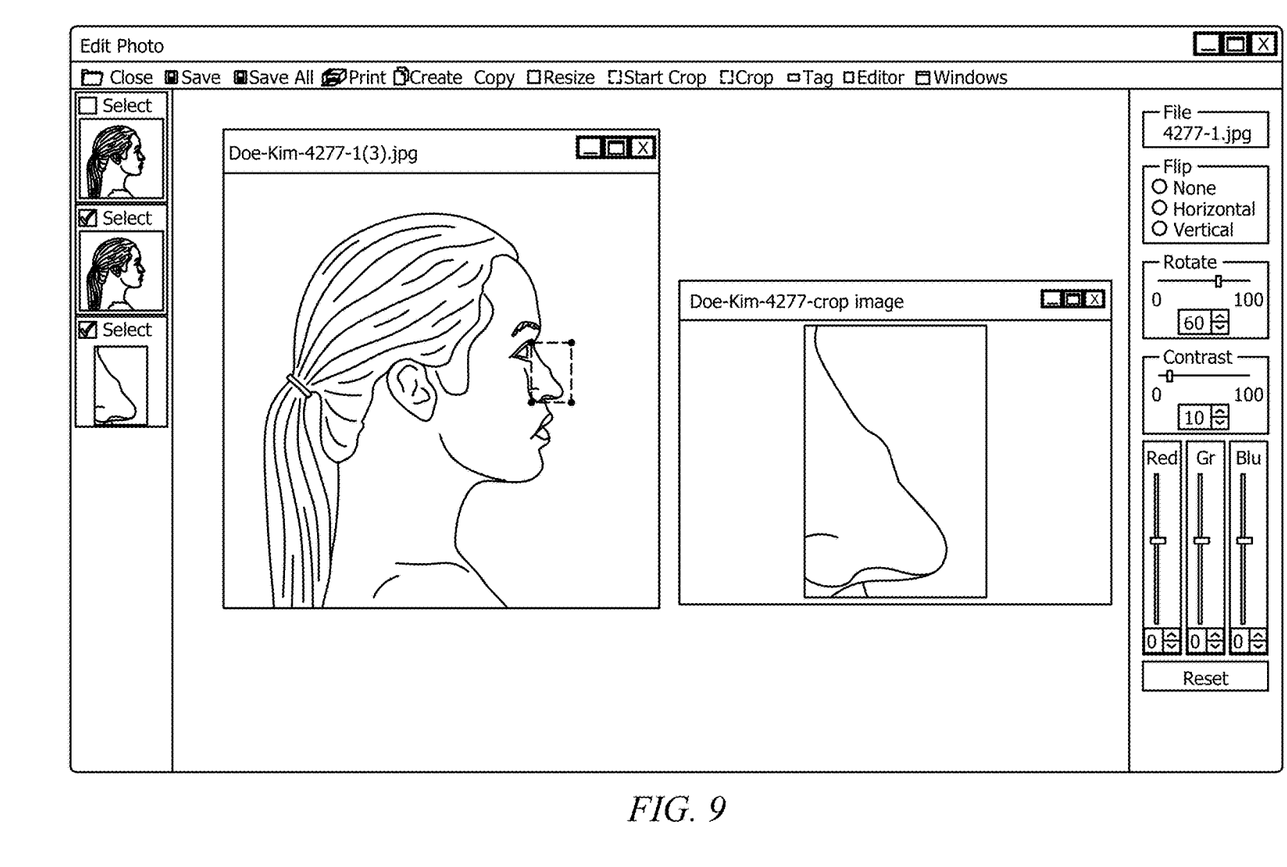
FIG. 9 is a screen shot showing an example of the image editing screen showing creating a partial image of an image according to an embodiment of the present invention.

Users are also able to crop images by picking specific points on a patient image, as illustrated in FIG. 9. Images can also be re-sized and their orientation can be changed. Images can also be resized simultaneously with a re-size slide bar, as shown in the upper left corner of FIG. 11.

Figures 10A, 10B:
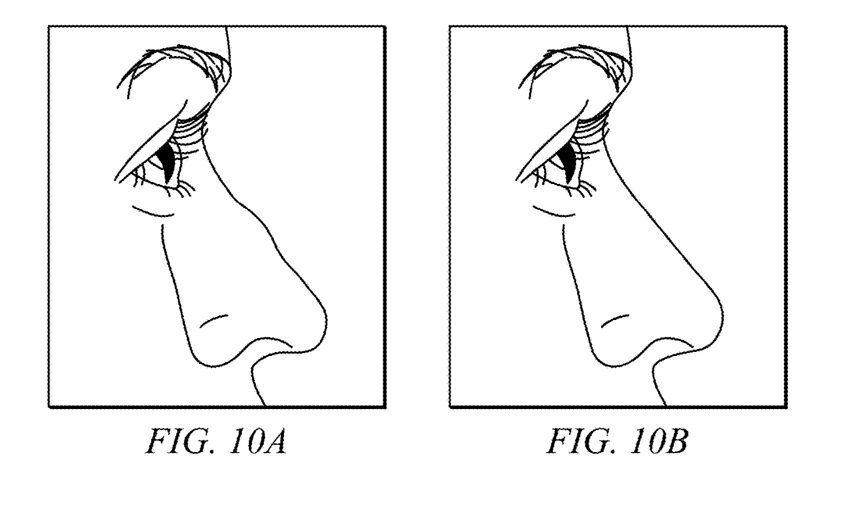
FIG. 10A is an example illustration of a pre-operative image.
FIG. 10B is an example illustration of a post-operative image.
Figure 10C:
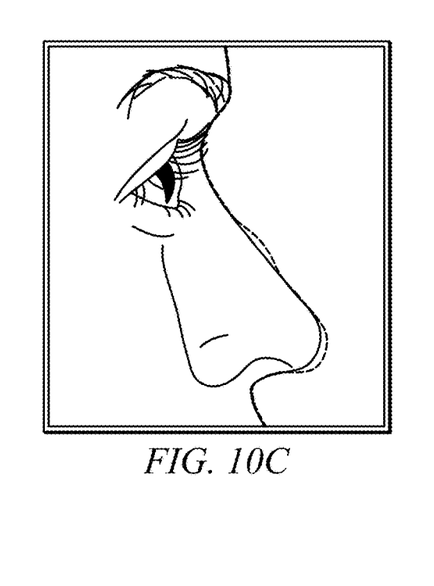
FIG. 10C is an example illustration of the product of the ghost overlay feature using the example illustrations of FIGS. 10A and 10B according to an embodiment of the present invention.

The patient image management system also includes a ghost overlay function. Two or more images are overlaid in order to visually demonstrate post surgical results. This feature is illustrated in FIGS. 10A through 10C. FIG. 10A shows a pre-op image and FIG. 10B shows a post-op image. FIG. 10C is a ghost overlay of the pre-op image and post-op images. The ghost overlay function allows a user to control the transparency of each image to effectively animate the transition from the pre-op and the post-op images. It provides the user dynamic transitional control to demonstrate exactly how a patient's contours have changed.

Figure 11:
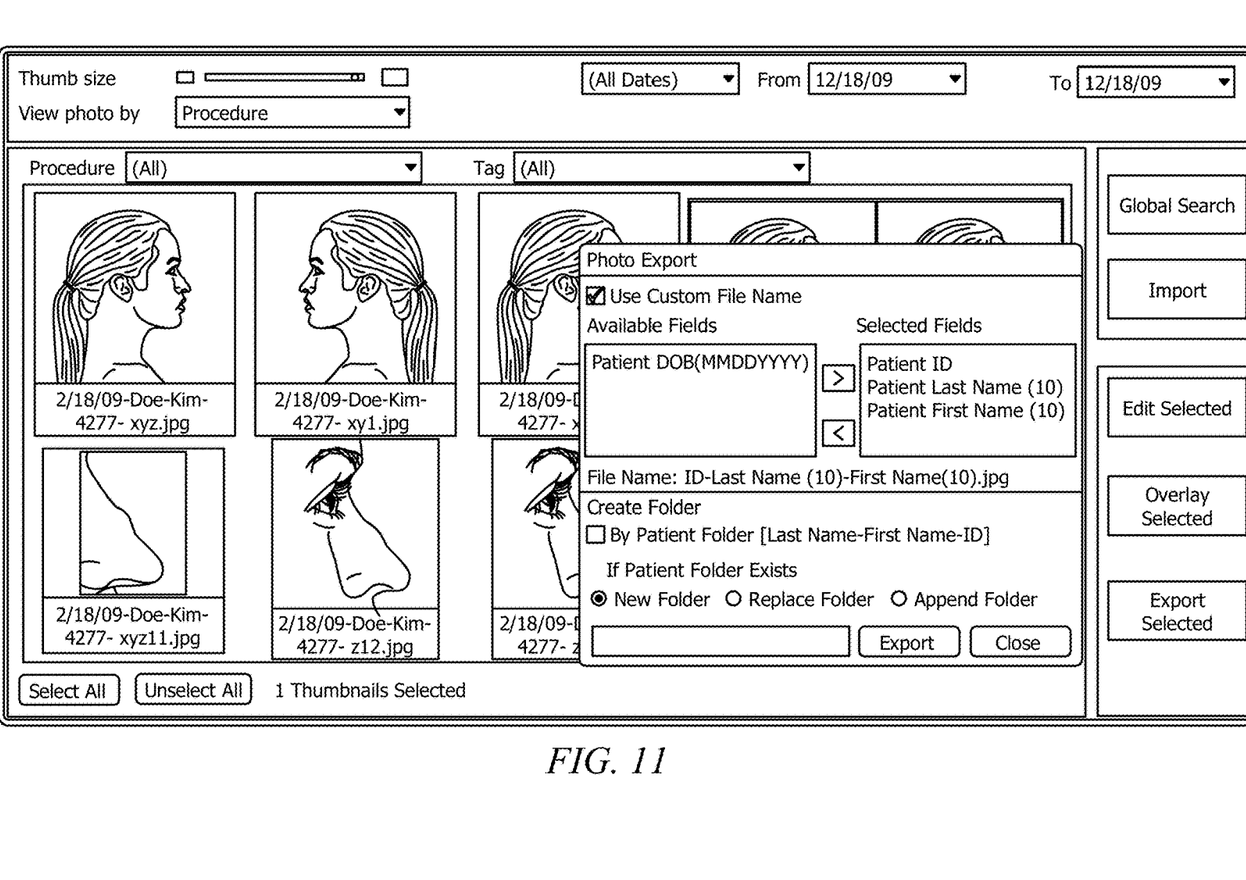
FIG. 11 is a screen shot showing an example of the patient file and illustrating the image exportation feature according to an embodiment of the present invention.
Figure 12:
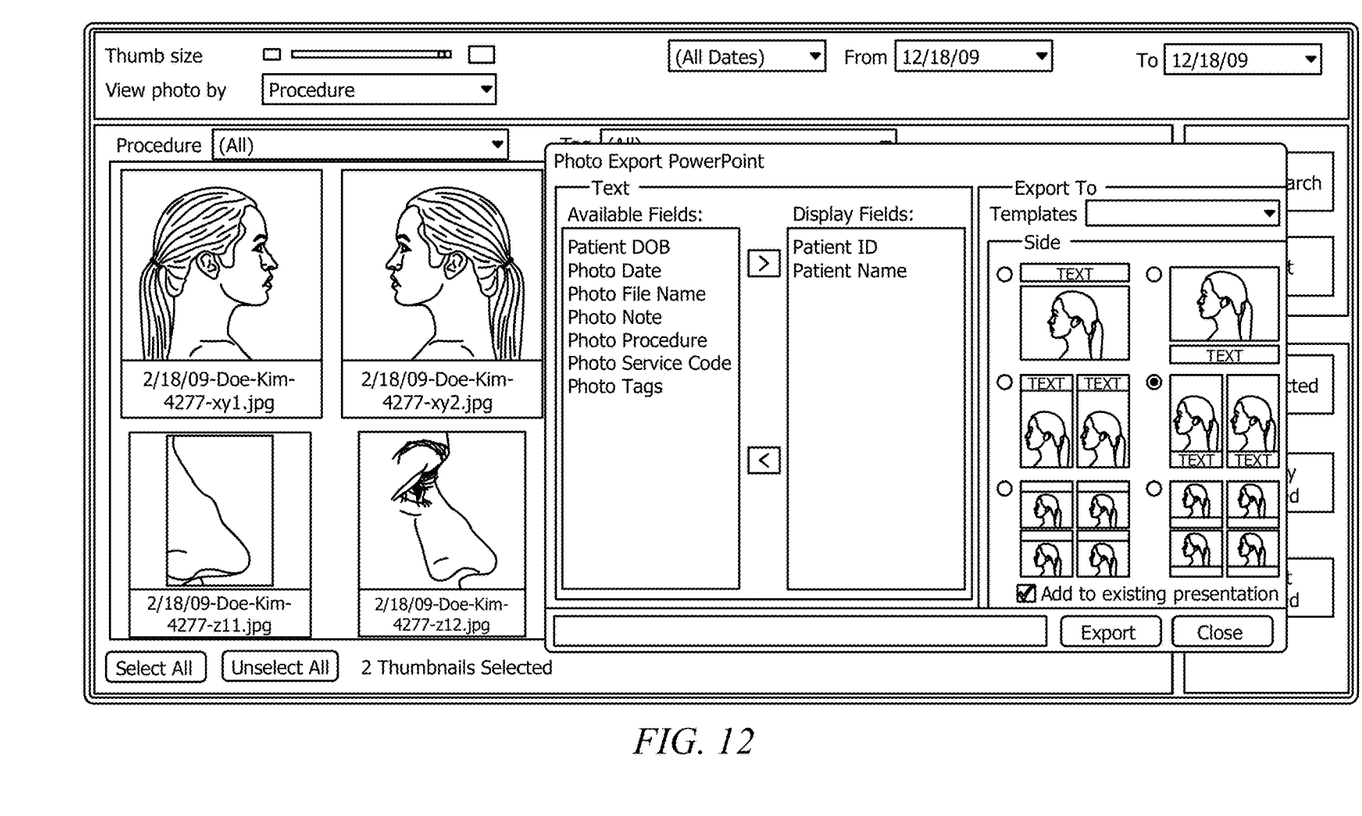
FIG. 12 is a screen shot showing an example of the patient file and further illustrating the image exportation feature according to an embodiment of the present invention.

The edited images, as well as existing images, can be saved directly to a patient's chart (or EMR), to a to-do task for staff to follow-up, to a patient's file, or exported to an encrypted email, the web, to other modules with a practice management system, or to applications such as Microsoft® Word, Microsoft® PowerPoint, and PDF Catalog Generator (pre-defined templates (shown in FIG. 12). FIGS. 11 and 12 illustrate the export function. For example, patient Jane Doe's rhinoplasty photos can be exported to her clinical chart for documentation, or to a staff's to-do task for a specific follow-up.

In addition, users are able to perform a global search of all patients based on procedure, tag, service code, patient group, and dates.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. One or more tangible non-transitory, computer-readable media having computer-executable instructions for performing a method of running a software program on a computing device, the computing device operating under an operating system, the method including issuing instructions from the software program for a computer processor to generate an integrative medical practice management system, the instructions comprising:
    receiving a plurality of digital images associated with a plurality of patients, the plurality of images containing an image having a file creation timestamp set by a digital imaging device, the image being a visible light imagery of portrait-framed external features of a patient selected from the plurality of patients, the timestamp comprising a date and time;
    receiving procedure information about one or more appointments attended by the patient, the procedure information having an assigned date;
    decoding the timestamp and automatically filtering a patient list based on the timestamp and scheduled appointments that have occurred on the timestamp;
    associating the image with the patient selected from the patient list as a result of an operator requesting the association, said association occurring only subsequent to the steps of receiving the plurality of images and procedure information and also subsequent to the step of the patient list and the scheduled appointments being filtered based the timestamp of the image;
    verifying whether the assigned date includes a value corresponding to the timestamp;
    automatically retrieving the procedure information and tagging the image of the patient with the procedure information as a result of a determination that the assigned date includes a value corresponding to the timestamp; and
    organizing the plurality of digital images by respective procedure using the procedure information of each of the digital images.

2. One or more media as in claim 1, further comprising:
    receiving service codes about the one or more appointments attended by the patient, the services codes having an additional assigned date;
    verifying whether the additional assigned date includes a value corresponding to the timestamp;
    automatically retrieving the service codes and tagging the image of the patient with the service codes as a result of a determination that the additional assigned date includes a value corresponding to the timestamp.

3. One or more media as in claim 2, further comprising:
    conducting a global search of the patient list based on at least one category selected from the group consisting of the procedure information, the tagged image, the service codes, a patient group to which any patient fhm1 the patient list may belong, the timestamp, and the additional assigned date.

4. One or more media as in claim 1, further comprising:
    tagging the image of the patient with a custom tag responsive to a request from the operator.

5. One or more media as in claim 1, further comprising:
    automatically generating a post-operative interval based on the procedure information associated with the image of the patient.

6. One or more media as in claim 1, further comprising:
    displaying the image of the patient in a film icon, the film icon comprising:
        a center image;
        a plurality of side images on at least one side of the film icon, each side image of the plurality of side images having a uniform size and each side image of the plurality of side images having a smaller size than the center image, aligned in a column on the at least one side of the film icon.

7. One or more media as in claim 1, further comprising:
    receiving an electronic medical record of the patient;
    automatically tagging the image of the patient with the electronic medical record of the patient as a result of a determination that the assigned date includes a value corresponding to the timestamp.

8. One or more media as in claim 1, further comprising:
    receiving an additional image having an additional assigned date, the image associated with the patient, the additional assigned date being a later date or time than the timestamp;
    overlaying the image with the additional image;
    altering the transparency of the image and the additional image to animate the transition from the image to the additional image;
    comparing the additional image to the image in order to determine medical progress of the patient; and
    scheduling a follow-up appointment for the patient based on the comparison of the additional image to the image.

9. One or more tangible non-transitory media having computer-executable instructions for performing a method of running a software program on a computing device, the computing device operating under an operating system, the method including issuing instructions from the software program for a computer processor to generate an integrative medical practice management system, the instructions comprising:

receiving a plurality of digital images, each image of the plurality of images having a file creation timestamp set by a digital imaging device, the plurality of images associated with a plurality of patients, said each image being a visible light imagery of portrait-framed external features of a patient selected from the plurality of patients, the timestamp comprising a date and time;

receiving a plurality of sets of procedure information about one or more appointments attended by the plurality of patients, each set of procedure information having an assigned date;

immediately decoding the timestamp and automatically filtering a patient list based on the timestamp and the one or more appointments that have occurred on the timestamp;

associating the each image of the plurality of images with the plurality of patients from the patient list as a result of an operator requesting the association, said association occurring only subsequent to the steps of receiving the plurality of images and receiving the procedure information and also subsequent to the step of the patient list and the scheduled appointments being filtered based the timestamp of the image;

verifying whether the assigned date includes a value corresponding to the timestamp;

for each image-patient association, automatically retrieving a corresponding set of procedure information and tagging the image of the patient with the corresponding set of procedure information as a result of a determination that the assigned date includes a value corresponding to the timestamp; and organizing the plurality of digital images by respective procedure using the procedure information of each of the digital images.

10. One or more media as in claim 9, further comprising:
receiving service codes about the one or more appointments attended by the each patient of the plurality of patients, the services codes having an additional assigned date;

verifying whether the additional assigned date includes a value corresponding to the timestamp; and for each image-patient association, automatically retrieving and tagging the image of the patient with the service codes as a result of a determination that the additional assigned date includes a value corresponding to the timestamp.

11. One or more media as in claim 10, further comprising:
conducting a global search of the patient list based on at least one category selected from the group consisting of the plurality of sets of procedure information, the tagged image of the patient in each image-patient association, the service codes, a patient group to which the one or more patients from the patient list may belong, the timestamp, and the additional assigned date.

12. One or more media as in claim 9, further comprising:
for each image-patient association, tagging the image of the patient with a custom tag responsive to a request from the operator.

13. One or more media as in claim 9, further comprising:
the procedure information further including at least one procedural category;
automatically organizing each image selected from the plurality of images by the at least one procedural category associated with each image selected from the plurality of images.

14. One or more media as in claim 9, further comprising:
said plurality of images including two or more images;
said one or more patients including one patient;
overlaying each image of the two or more images on top of each other; adjusting the transparency of the two or more images to animate the differences between the two or more images;
comparing the two or more images in order to determine medical progress of the one patient; and
scheduling a follow-up appointment for the one patient based on the comparison of the two or more images.

* * * * *